United States Patent
Kroll

[19]

[11] Patent Number: 5,814,075
[45] Date of Patent: Sep. 29, 1998

[54] METHOD AND APPARATUS FOR OPTIMIZING SOURCE ALLOCATION WITHIN AN IMPLANTABLE CARDIOVERTER-DEFIBRILLATOR

[75] Inventor: Mark W. Kroll, Simi Valley, Calif.

[73] Assignee: Pacesetter, Inc., Sylmar, Calif.

[21] Appl. No.: 877,046

[22] Filed: Jun. 17, 1997

[51] Int. Cl.$^6$ ...................................................... A61N 1/39
[52] U.S. Cl. ................................................ 607/5; 607/34
[58] Field of Search ...................................... 607/34, 5, 9

[56] References Cited

U.S. PATENT DOCUMENTS

| | | | |
|---|---|---|---|
| 3,882,322 | 5/1975 | Gobeli | 607/34 |
| 4,096,866 | 6/1978 | Fischell | 607/34 |
| 4,120,306 | 10/1978 | Renirie | 607/34 |
| 5,372,605 | 12/1994 | Adams et al. | 607/34 |

Primary Examiner—William E. Kamm

[57] ABSTRACT

A power control system is described for use in an implantable cardioverter-defibrillator (ICD) having a low-power cell and a high-power cell. The power control system includes a fuzzy logic controller for gradually varying the relative amounts of energy drawn from the low- and high-power cells based upon a selected function to be performed by the ICD and upon various operational parameters of the ICD. Example functions include cardioversion therapy, cardiac defibrillation, cardiac pacing, cardiac monitoring and capacitor reformation. Example operational parameters include the remaining capacities of the low- and high-power cells, the amount of time since implant of the ICD, the number of defibrillation shocks already delivered, and the amount of pacing energy previously utilized. In each case, the fuzzy logic controller applies a set of fuzzy logic rules to determine the relative amounts of energy to be drawn from the two power cells to optimize energy source allocation and to extend the overall longevity of the ICD.

24 Claims, 11 Drawing Sheets

METHOD AND APPARATUS FOR OPTIMIZING SOURCE ALLOCATION WITHIN AN IMPLANTABLE CARDIOVERTER-DEFIBRILLATOR

FIELD OF THE INVENTION

The invention generally relates to implantable medical devices and in particular to implantable cardioverter-defibrillator (ICD) devices having two or more different energy sources.

BACKGROUND OF THE INVENTION

An ICD is a device for implantation within the body that is capable of recognizing ventricular tachycardia or ventricular fibrillation and for delivering electrical therapy to terminate such arrhythmias. ICD's are often configured to also perform pacemaking functions as well.

Special difficulties arise in providing an adequate energy source for ICD's, particularly those that are also intended to perform pacemaking functions. Cardioversion-defibrillation typically requires a few high-power electrical shocks to be generated relatively infrequently. For cardioversion, the shocks are typically at about two joules. For defibrillation, the shocks are typically at about twenty joules. Pacemaking functions, in contrast, may require that numerous relatively low-power electrical shocks be generated frequently. Pacing shocks are typically on the order of micro-joules. Energy is also required to monitor the heart for the purposes of detecting when cardioversion, defibrillation or pacing is required. Monitoring causes a continuous low-power current draw of about ten microamperes.

Also, energy may be required to reform whatever capacitor is used in connection with delivering defibrillation shocks. In this regard, aluminum electrolytic capacitors, which are commonly employed, typically must be charged to full voltage every couple of months to prevent degradation. Whether energy is actually required to perform capacitor reformation depends upon whether the patient receives relatively frequent defibrillation shocks. The ICD's of patients that do not receive at least one defibrillation shock every month or two will require a periodic capacitor reformation cycle. The ICD's of patients that do receive at least one defibrillation shocks every month or two, however, do not typically require capacitor reformation cycles because reformation is achieved automatically during the generation of the defibrillation shocks.

To accommodate these various energy requirements, some ICD designs employ two power cells-a high-power cell and a low-power cell. Exemplary high-power cells include manganese dioxide cells and silver vanadium oxide (SVO) cells. Exemplary low-power cells include carbon monofluoride cells ($CF_x$) and lithium iodine cells. In one possible example, the high-power cell provides energy for capacitor reformation and for cardioverter-defibrillator functions and the low-power cell provides energy for the pacemaking and monitoring functions. In other possible examples, the high-power cell provides energy for capacitor reformation, cardioverter-defibrillator functions and pacemaking functions and the low-power cell provides energy only for the monitoring functions.

The simplest ICD devices having separate high-power and low-power cells performed only monitoring, pacing and defibrillation functions and were configured to always draw energy for defibrillation from the high-power cell and to always draw energy for pacing and monitoring from the low-power cell i.e. the power cells are non-switchable. However, the actual energy drawn from the low- and high-power sources varies considerably from patient to patient. For example, some patients require frequent pacing but little or no defibrillation whereas other patients require relatively frequent defibrillation but little or no pacing. Still others require neither pacing nor defibrillation but merely require continuous monitoring.

As a result of the wide variations in actual energy usage, circumstances can arise within non-switchable ICD's wherein one power cell becomes quickly depleted thereby necessitating early replacement of the ICD even though the other power cell retains considerable energy and could otherwise continue to energy the ICD. For example, circumstances can arise wherein the ICD must be replaced because the low-power cell has been depleted from frequent pacing or from a long period of continuous monitoring even though the high-power cell has abundant energy and could otherwise continue to energy all ICD functions.

More sophisticated devices switch from the low-power cell to the high-power cell if the low-power cell becomes depleted. An example is described in U.S. Pat. No. 5,372,605, to Adams, wherein energy for pacing and defibrillation is drawn from an SVO cell and energy for monitoring is drawn from a lithium iodine cell. With the Adams technique, energy for monitoring is switched from the lithium iodine cell to the SVO cell if the lithium iodine cell becomes depleted.

Although the Adams technique represents an improvement over non-switchable systems, substantial room for further improvement remains. For example, with the Adams technique, if the patient requires a considerable amount of pacing and a considerable amount of defibrillation therapy, the SVO cell will become quickly depleted thereby necessitating early replacement of the device even though the lithium iodine cell retains considerable energy reserves. In such circumstances, it would be preferable to switch the device, while the SVO cell still retains sufficient energy for defibrillation, to draw energy for the pacemaking functions from the lithium iodine cell to thereby slow the depletion of the SVO cell by more effectively using the remaining energy of the lithium iodine cell. However, the Adams technique does not provide for switching from the high-power cell to the low-power cell and thereby may result in a premature replacement of the ICD. Moreover, even the manner by which the Adams technique operates to switch from the low-power cell to the high-power cell could be improved. In this regard, the Adams technique merely operates to determine whether the low-power cell has become completely depleted and, if so, switches completely and immediately to the high-power cell. Further improvement can be gained by gradually adjusting the relative amounts of energy drawn from the two power cells in an optimal manner.

Moreover, the Adams technique and other simple switching techniques do not account for various other factors which can affect the optimal manner by which energy is drawn from two or more power cells. For example, SVO cells begin to lose their effectiveness with age, even if unused. Hence, even for powering functions that could otherwise be powered by a low-power cell, it would be preferable to begin to draw greater amounts of energy from the high-power SVO cell than from the low-power cell as the number of years since implant increases. Also the Adams technique does not account for the need, if any, to perform capacitor reformation. Nor does the Adams technique account for that actual amount of energy previously used for pacing or the number of defibrillation shocks previously delivered, both of which can affect the optimal manner by which remaining amounts of power should be drawn from the two power cells.

Accordingly, it would be desirable to provide a more intelligent approach to drawing energy from two or more energy sources within an ICD that accounts for the aforementioned factors to maximize the usable life of an ICD and it is to that end that aspects of the present invention are drawn.

SUMMARY OF THE INVENTION

In accordance with one aspect of the invention, a power control system is provided for an implantable medical device having two or more energy sources for powering two or more device functions. The power control system includes a means for receiving signals representative of an operational status of the implantable medical device; a means for biasing relative amounts of energy drawn from the two or more different energy sources; and a means for controlling the means for biasing to gradually vary the relative amounts of energy drawn from the two or more different energy sources based upon the signals representative of the operational status of the implantable medical device.

In an exemplary embodiment, the implantable medical device is an ICD capable of performing cardioversion therapy, cardiac defibrillation, cardiac pacing, cardiac monitoring and capacitor reformation. First and second power cells are provided, with the first cell being a low-power cell optimized for providing a continuous source of low-power for cardiac monitoring and the second cell being a high-power cell optimized for providing brief and infrequent bursts of high-power for cardiac defibrillation. In the exemplary embodiment, the means for controlling applies fuzzy logic to the signals representative of the operational status of the ICD to control the means for biasing to gradually adjust the relative amounts of energy drawn from the first and second power cells. In one specific example, the following fuzzy logic rules are applied:

a) defibrillation shocks are simultaneously drawn from the first and second power cells unless the remaining capacity of the first power cell is much less than that of the second power cell;

b) a greater amount of energy is drawn from the second power cell than from the first power cell if the number of years since implant is high;

c) a greater amount of energy is drawn from the first power cell than from the second power cell if the number of defibrillation shocks is high;

d) energy is alternatingly drawn from the first and second cells for capacitor reformation and for cardioversion therapy during the first few years since implant;

e) monitoring energy is drawn from the first cell during the first few years after implantation or when the remaining capacity of the first cell is significantly greater than that of the second cell;

f) pacing energy is drawn from the first cell when relatively little pacing energy has been used or if the remaining capacity of the first cell is significantly greater than that of the second cell.

Method embodiments of the invention are also provided.

BRIEF DESCRIPTION OF THE DRAWINGS

These and other features of the invention will be described in connection with the accompanying drawings in which like reference numerals represent like components throughout and in which.

DETAILED DESCRIPTION OF THE INVENTION

The invention relates to systems and methods for controlling the relative amounts of energy drawn from two or more energy sources within an implantable medical device. The invention will be described primarily with reference to an ICD having two power cells but principles of the invention may also be applicable to other implantable medical devices having two or more energy sources as well.

Figure 1:
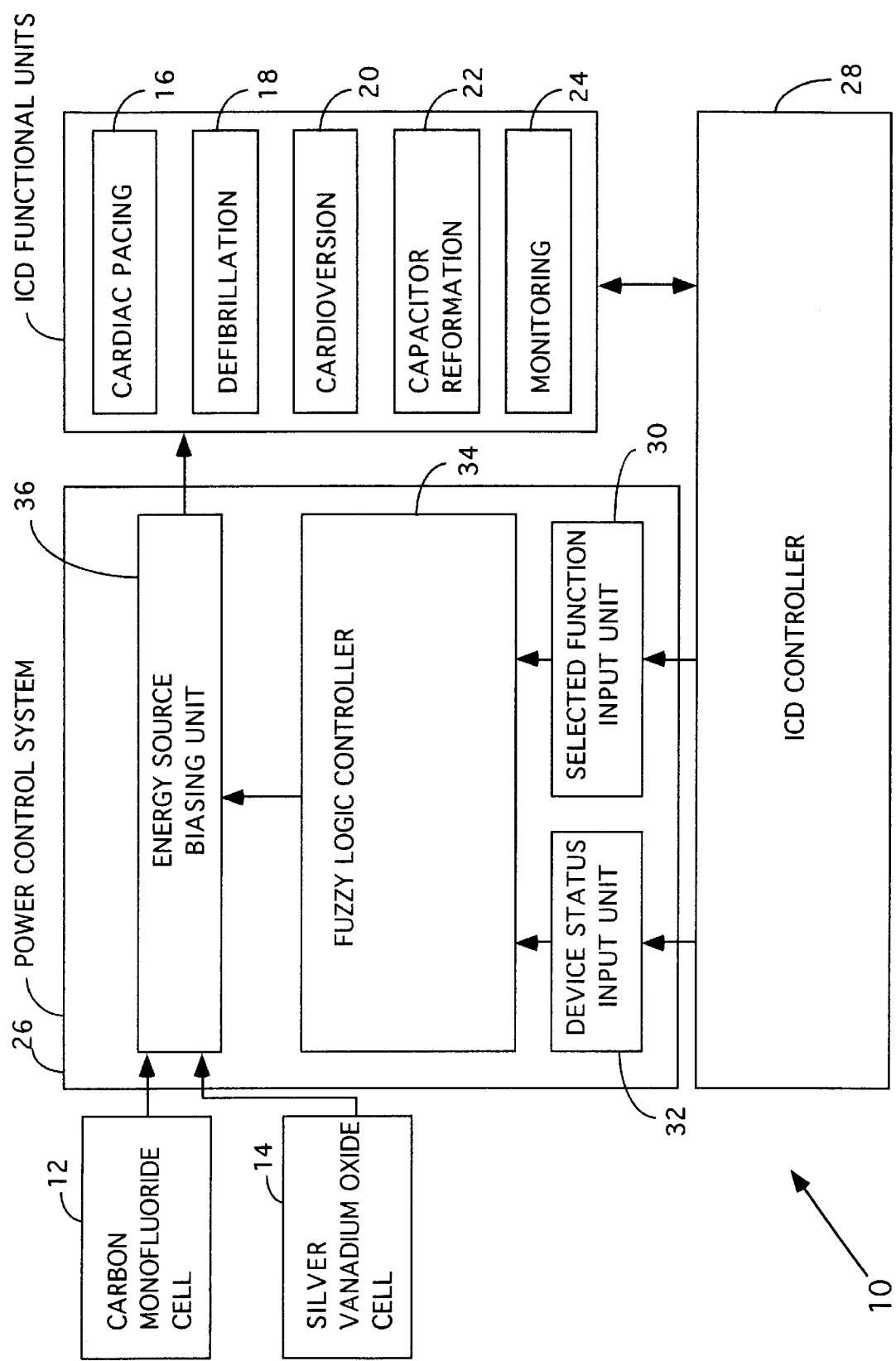
FIG. 1 is block diagram of an ICD configured in accordance with an exemplary embodiment of the invention and having a power control system employing fuzzy logic for gradually adjusting the relative amounts of energy drawn from a pair of power cells including a $CF_x$ cell and a SVO cell.

FIG. 1 is a block diagram illustrating functional components of an ICD 10 having a pair of energy sources (specifically, a $CF_x$ cell 12 and an SVO cell 14) for powering various functional units of the ICD including a cardiac pacing unit 16, a defibrillation unit 18, a cardioversion unit 20, a capacitor reformation unit 22 and a monitoring unit 24. Energy is selectively drawn from the pair of energy sources 12 and 14 by a power control system 26 which gradually adjusts the relative amounts of energy drawn from the SVO and $CF_x$ cells in a manner intended to optimize energy usage to achieve the greatest longevity of the ICD before it must be replaced as a result of depletion of the power cells. For example, for defibrillation, power control system 26 operates to initially draw energy simultaneously from the SVO and $CF_x$ cells in a 90%/10% ratio and to gradually draw an increasing percentage of energy for defibrillation from the SVO cell as energy from the $CF_x$ cell becomes depleted. As another example, the power control system operates to initially draw all energy from the $CF_x$ cell for cardiac pacing but gradually begins to also draw a portion of the energy for pacing from the SVO cell.

As will be described further, power control system 26 employs fuzzy logic to determine the relative amounts of energy to be drawn from the SVO and $CF_x$ cells based upon the specific function that is being powered and upon various operational parameters of the ICD, such as the remaining capacities of the power cells, the number of years since implant of the ICD, the amount of pacing energy already utilized, and the number of defibrillation shocks already delivered.

As noted, the ICD operates to perform any or all of the following functions: cardiac pacing, defibrillation, cardioversion, capacitor reformation and monitoring. Briefly, monitoring unit 24 operates substantially continuously to monitor the activity of the heart of a patient in which the ICD is implanted (using a pacing/sensing electrode not shown). Data measured by the monitoring unit is forwarded to an ICD controller 28 which processes the data to determine if therapy is required and, depending upon the therapy needed, triggers operation of either cardiac pacing unit 16, defibrillation unit 18 or cardioversion unit 20. Cardiac pacing involves generating mild electric shocks on the order of a few dozen micro-joules each within the heart in an attempt to remedy various heart arrhythmias such as tachyarrhythmias or bradyarrhythmias. Cardioversion involves generating much more significant electrical shocks of about two joules each in an attempt to terminate ventricular tachycardia or atrial tachyarrhythmia. Defibrillation involves generating even more significant electrical shocks of about twenty joules each in an attempt to terminate ventricular fibrillation. ICD controller 28 may also trigger a capacitor reformation operation every month or two wherein a capacitor (not shown) used in connection with defibrillation or cardioversion is charged to thereby prevent deposition of a thin film on a cathode of the capacitor which may otherwise occur if the capacitor is not charged as a result of generating cardioversion or defibrillation shocks. The manner by which these various functions are performed may be entirely conventional and will not be described further. Also the manner by which ICD controller 28 operates to trigger and otherwise control the functions may be entirely conventional.

ICD controller 28 additionally tracks operational parameters of the ICD including the remaining capacities of the SVO and $CF_x$ cells, the number of years since implant of the ICD, the number of defibrillation shocks delivered and the amount of pacing energy utilized by the cardiac pacing unit. An estimation of the remaining capacities of the SVO and $CF_x$ cells is achieved by any appropriate technique such as by measuring the voltages of the cells. In this regard, although not shown, ICD controller 28 may be directly connected to the SVO and $CF_x$ cells for measuring the remaining capacities thereof. Tracking of the number of years since implant and the number of defibrillation shocks delivered is achieved by ICD controller 28 through use of simple counters. Tracking of the amount of pacing energy utilized is likewise achieved by using a suitable counter and by factoring in the actual or average amounts of energy used per pacing pulse.

To allow power control system 26 to control the relative amounts of energy to be drawn from the SVO and $CF_x$ cells for any particular function, ICD controller 28 forwards a signal representative of the functional unit requiring energy to a selected function input unit 30 of power control system 26 and forwards signals representative of one or more of the aforementioned operational parameters to a device status input unit 32 also of the power control system. The input units forward the respective input signals to a fuzzy logic controller 34 which processes the input signals using preprogrammed fuzzy logic rules and generates a bias control signal representative of the relative amounts of energy to be drawn from the two power cells based upon the selected function and the operational parameters. The control signal may indicate, for example, that energy for the selected function is to be drawn only from the SVO cell, only from the $CF_x$ cell or from both cells at a selected ratio. As can be appreciated, a wide variety of techniques may be employed for parameterizing the bias control signal. In the exemplary embodiment presently described, the bias control signal is parameterized by a numeric value ($bias_{control}$) ranging from 0 to 100 with 0 indicating that energy is to be drawn exclusively from the $CF_x$ cell, 100 indicating that energy is to be drawn exclusively from the SVO cell and values therebetween indicating relative percentages. For example, a $bias_{control}$ value of 78 indicates that 78 percent of the energy is to be drawn from the SVO cell and the remaining 22 percent is to be drawn from the $CF_x$ cell. A power control signal representative of $bias_{control}$ is then forwarded to an energy source biasing unit 36 which operates to bias the energy drawn from the two power cells in accordance with $bias_{control}$ and to feed the energy to the appropriate functional unit that needs to be powered.

Thus fuzzy logic controller 32 operates to generate a power control signal based upon a selected device function and upon current operational parameters of the ICD using fuzzy logic. More specifically, the fuzzy logic controller applies the following basic fuzzy logic rules to the input signals to generate the power control signal:

Rule 1: defibrillation shocks are simultaneously drawn from the SVO and $CF_x$ cells unless the remaining capacity of the $CF_x$ cell is much less than that of the SVO cell;

Rule 2: a greater amount of energy is drawn from the SVO cell than from the $CF_x$ cell if the amount of time since implant is high;

Rule 3: a greater amount of energy is drawn from the $CF_x$ cell than from the SVO cell if the number of defibrillation shocks previously delivered is high;

Rule 4: energy is alternatingly drawn from the $CF_x$ and SVO cells for capacitor reformation and for cardioversion therapy during the first few years since implant;

Rule 5: monitoring energy is drawn from the $CF_x$ cell during the first few years after implantation or when the remaining capacity of the $CF_x$ cell is significantly greater than that of the SVO cell; and Rule 6: pacing energy is drawn from the $CF_x$ cell when relatively little pacing energy has been used or if the remaining capacity of the $CF_x$ cell is significantly greater than that of the SVO cell.

The fuzzy logic rules will be further described with reference to the flowcharts of FIGS. 2–7.

Figure 2:
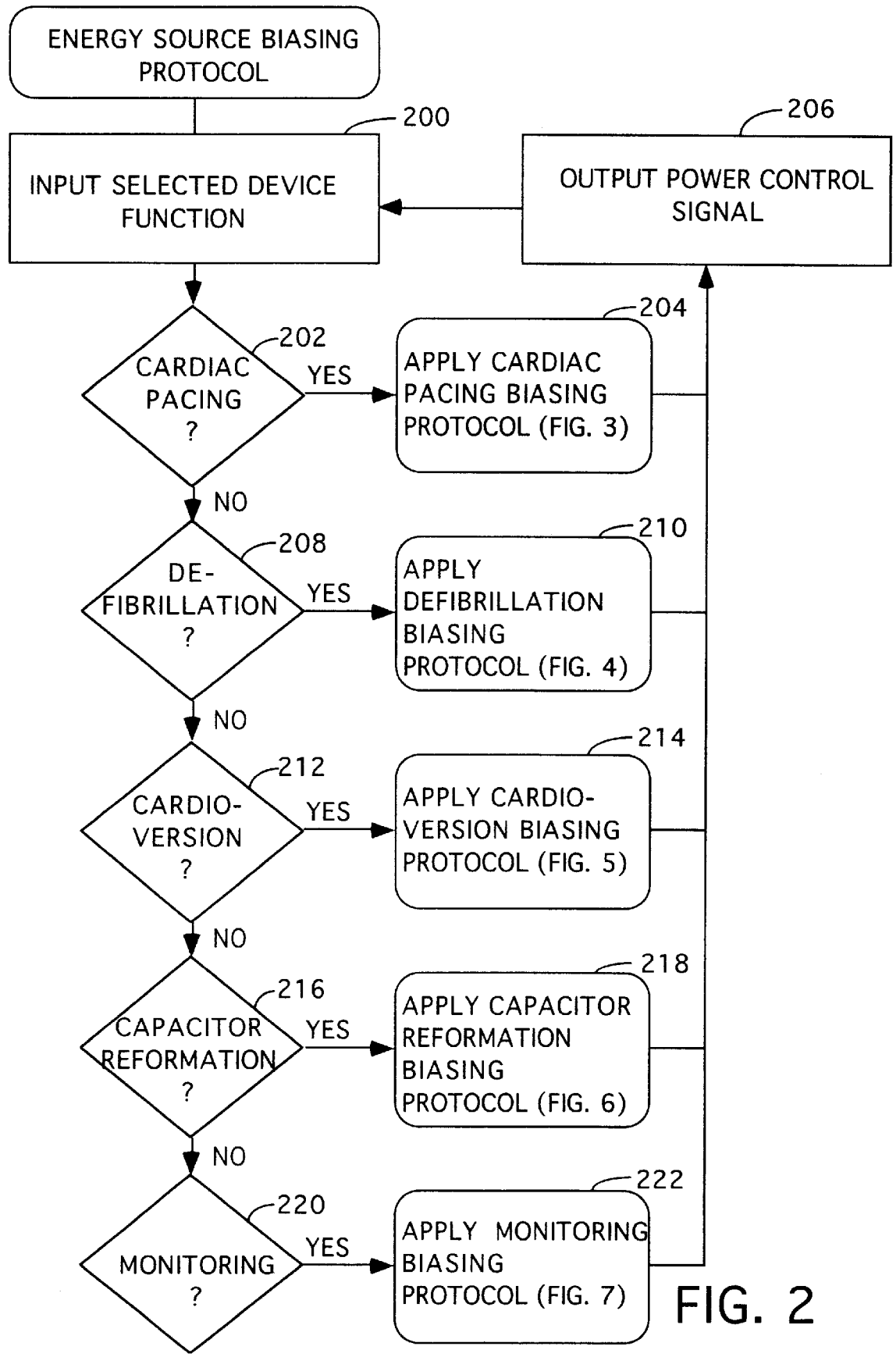
FIG. 2 is a flow chart illustrating steps performed by the power control system of FIG. 1 for selecting and controlling the relative amounts of energy to be drawn from the pair of power cells for powering a variety of ICD functions.

FIG. 2 illustrates, at a high level, an energy source biasing protocol performed by fuzzy logic controller 34 (FIG. 1).

Initially, at step 200, a signal identifying a selected device function is received which identifies either cardiac pacing, defibrillation, cardioversion, capacitor reformation or monitoring. If cardiac pacing is selected then, from step 202, execution proceeds to step 204 wherein an energy biasing protocol is implemented as shown in FIG. 3 which applies fuzzy logic Rules 2, 3 and 6 (listed above) to generates a power control signal appropriate for pacing.

Figure 3:
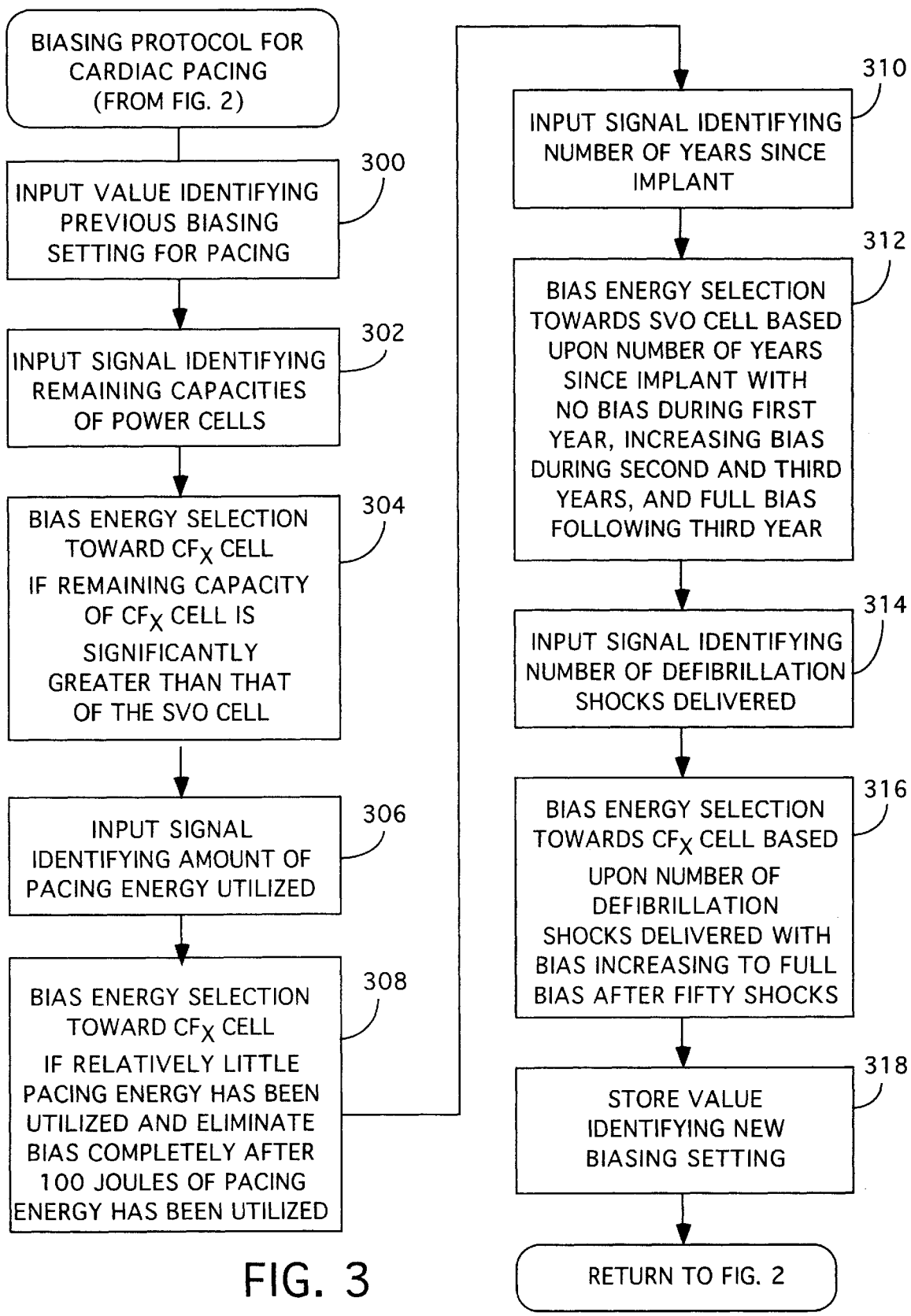
FIG. 3 is a flow chart illustrating particular steps performed for selecting and controlling the relative amounts of energy to be drawn from the pair of power cells for powering cardiac pacing functions.

At step 300 of FIG. 3, a signal identifying a previous biasing value $bias_{pacing}$ for cardiac pacing is retrieved from a memory (not separately shown) within the fuzzy logic controller. The first time the steps of FIG. 3 are performed (i.e. the first time pacing is required), the value of $bias_{pacing}$ is preset to a default value of 0 (indicating that all energy is to be drawn from the $CF_x$ cell). Subsequently, $bias_{pacing}$ may be adjusted in accordance with the remaining steps of FIG. 3 to range anywhere between 0 and 100.

At step 302, a signal is input identifying the remaining capacities of the $CF_x$ and SVO power cells. At step 304, energy source selection is biased toward the $CF_x$ cell if the remaining capacity of the $CF_x$ cell is significantly greater than that of the SVO cell. This adjustment is primarily performed to prevent the SVO cell from being prematurely depleted as a result of powering pacing functions that can otherwise be powered by the $CF_x$ cell. To this end, the numeric value of $bias_{pacing}$ is adjusted toward 0. For example, if the previous value of $bias_{pacing}$ was 24 and the remaining capacity of the $CF_x$ cell exceeds that of the SVO cell by a factor of two, step 304 may operate to reset $bias_{pacing}$ to, for example, 12 thereby specifying that a greater percentage of energy is to be drawn from the $CF_x$ cell. (Of course, if $bias_{pacing}$ is already set to 0, no further biasing toward the $CF_x$ cell is possible or necessary.)

The amount by which $bias_{pacing}$ is adjusted depends upon the extent to which the remaining capacity of the $CF_x$ cell exceeds that of the SVO cell. The greater the disparity in remaining capacities, the greater the adjustment to $bias_{pacing}$. Preferably, fuzzy logic techniques are employed to select the numerical adjustment, if any, to $bias_{pacing}$ based upon the previous value of $bias_{pacing}$, the relative capacities of the power cells and preprogrammed adjustment factors. The adjustment factors are set to values intended to optimize the longevity of the ICD. The adjustment factors may be set in accordance with theoretically optimum factors, if known, or may be determined empirically either by using computer simulation techniques or by measuring the relative longevity of actual power cells within ICD's having differing adjustment factors and by selecting those factors that yield the greatest resulting longevity. Also, depending upon the implementation, the adjustment factors may be adaptively varied while the ICD is in use. In still other implementations, fuzzy logic is not employed. Rather, simple Boolean or discrete logic is employed to adjust $bias_{pacing}$ by a fixed predetermined amount by, for example, subtracting the fixed amount from $bias_{pacing}$ if the capacity of the $CF_x$ cell is twice that of the SVO cell and by performing no adjustment otherwise.

Thus, steps 302 and 304 are performed to adjust $bias_{pacing}$ to a new value if the remaining capacity of the $CF_x$ cell is significantly greater than that of the SVO cell. Next, steps 306 and 308 are performed to further adjust $bias_{pacing}$ if relatively little pacing energy has been previously been utilized. Again this adjustment is provided primarily to prevent the SVO cell from being prematurely depleted as a result of powering pacing functions that can otherwise be powered by the $CF_x$ cell. More specifically, at step 306, a signal representing the amount of pacing energy that has previously been utilized is input. At step 308, $bias_{pacing}$ is adjusted toward 0 in inverse proportion to the amount of pacing energy utilized. No adjustment is made if over 100 joules of pacing energy has been utilized. Thus, for example, if the previous value of $bias_{pacing}$ was 10 as set by step 304 and no pacing energy has yet been utilized, then step 308 may operate to reset $bias_{pacing}$ to, for example, 5 to thereby specify that a still greater percentage of energy is to be drawn from the $CF_x$ cell. Fuzzy logic techniques are preferably employed to select the exact numerical adjustment, if any, to $bias_{pacing}$ based upon the previous value of $bias_{pacing}$, the amount of pacing energy previously utilized and preprogrammed adjustment factors. The adjustment factors used in step 308 likely differ from those used in step 304. As before, the adjustment factors are set to values intended to achieve the greatest longevity of the ICD and may be preprogrammed based upon optimal theoretical values or based upon empirically determined values. Also, as before, the adjustment factors may be adaptively varied. Further, Boolean or discrete logic may be alternatively employed instead of fuzzy logic.

At step 310, a signal identifying the number of years since implant of the ICD is received and, at step 312, energy source selection is biased toward the SVO cell based upon the number of years since implant. This adjustment is provided primarily to ensure that at least some energy for pacing is drawn from the SVO cell before the SVO cell, merely as a result of age, begins to lose power. To this end, $bias_{pacing}$ is adjusted toward 100 depending upon the amount of time since implant with no adjustment during the first year since implant, an increasing adjustment during the second and third years, and the greatest adjustment following the third year. Thus, if the value of $bias_{pacing}$ was previously set to 5 and the number of years since implant is two, step 312 may operate to adjust $bias_{pacing}$ up to, for example, 15. Again fuzzy logic techniques may be employed to operate in accordance with predetermined adjustment factors set to values intended to optimize ICD longevity.

At step 314, a signal identifying the number of defibrillation shocks delivered is received. At step 316, $bias_{pacing}$ is adjusted toward 0 to bias energy source selection toward the $CF_x$ cell based on the number of defibrillation shocks previously delivered, with no bias at zero shocks and an increasing bias as the number of shocks increases up to fifty. Thus, if the value of $bias_{pacing}$ was previously set to 15 and the number of defibrillation shocks delivered is 35, step 316 may operate to adjust $bias_{pacing}$ downwardly again to, for example, 8. Again fuzzy logic techniques may be employed to operate in accordance with predetermined adjustment factors.

At step 318, the value of $bias_{control}$, (discussed above in connection with FIG. 1) is set equal to that of $bias_{pacing}$. Also, the value of $bias_{pacing}$ is stored so that the next time the steps of FIG. 3 are executed, biasing will commence using the updated value for $bias_{pacing}$. Execution then proceeds to 206 of FIG. 2 wherein $bias_{control}$ is output by fuzzy logic controller 34 (FIG. 1) to energy source biasing unit 36 for controlling the relative amounts of energy to be drawn from the two power cells. Thus if, after the various adjustments of FIG. 3 have been performed, $bias_{control}$ is ultimately set to a value of 8, then 8% of the energy for the selected pacing operation is drawn from the SVO cell and 92% is drawn from the $CF_x$ cell.

Execution then returns to step 200 for receipt of a new selected function. If pacing is again selected, the aforementioned steps of FIGS. 2 and 3 are repeated to further adjust $bias_{pacing}$ as needed, ultimately yielding a new value for use as $bias_{control}$. In this manner, the value of $bias_{pacing}$ (and therefore also $bias_{control}$) is iteratively adjusted whenever pacing is required in an effort to bias the energy drawn from the pair of energy sources in an optimum manner to achieve the greatest longevity of the ICD. As will be explained below, adjustment for pacing need not be performed each and every time pacing is required. Rather, adjustment for pacing may be performed only periodically, such as every day or perhaps every 1000 pacing cycles.

What has just been described are biasing operations performed to biasing energy draw from the pair of power cells for use in powering pacing functions. Similar biasing operations are performed for each of the other selectable functions. In each case, a pre-stored $bias_{function}$ value (i.e. $bias_{defibrillation}$, $bias_{cardioversion}$ etc.) is retrieved from memory and adjusted in accordance with fuzzy logic techniques using pre-determined adjustment factors set to values intended to optimize ICD longevity. The biasing operations performed for these other ICD functions are similar to those employed for the pacing function just described and, for the sake of brevity, only pertinent differences will be described in detail.

Figure 4:
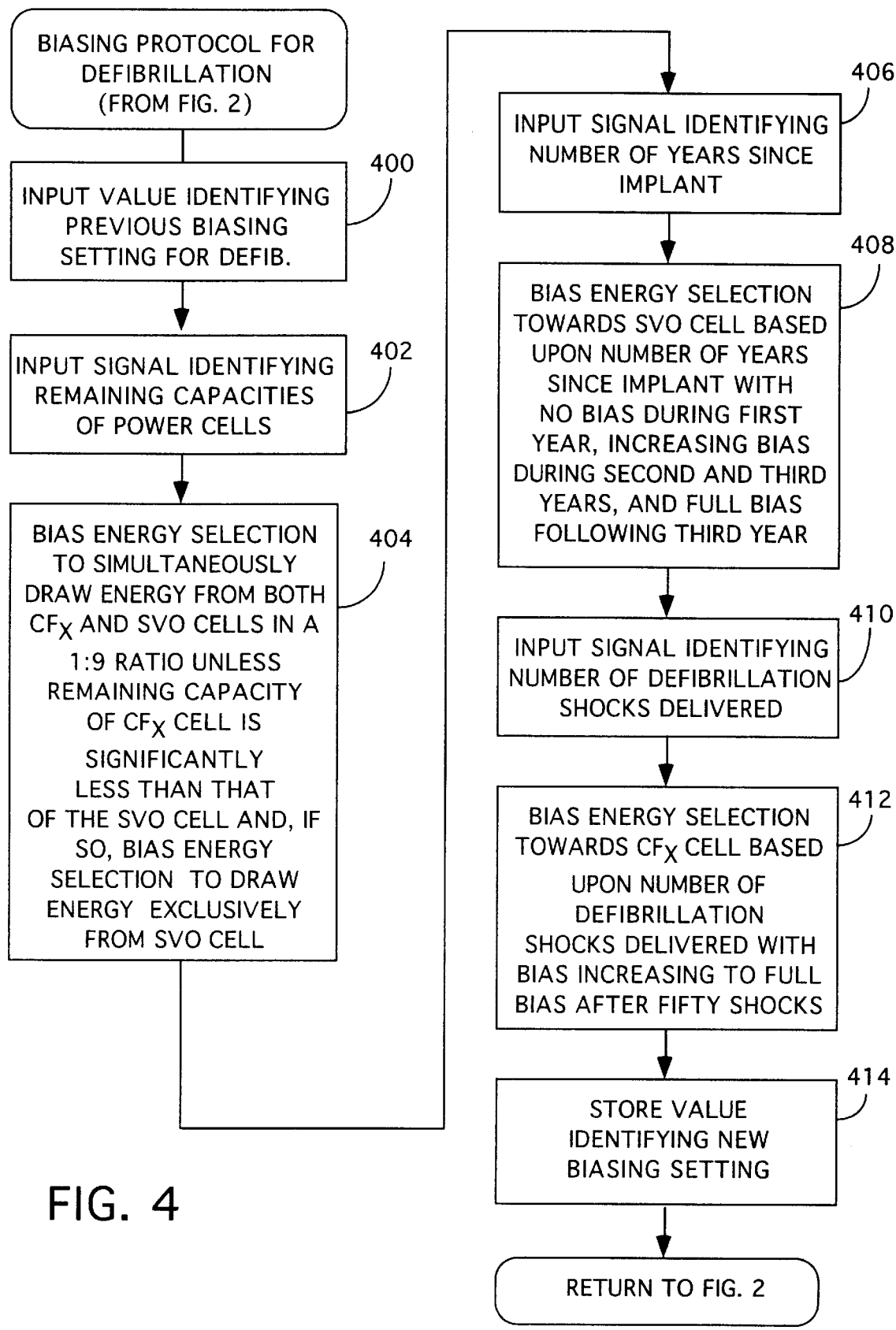
FIG. 4 is a flow chart illustrating particular steps performed for selecting and controlling the relative amounts of energy to be drawn from the pair of power cells for powering defibrillation functions.

If defibrillation is selected then, from step 208 of FIG. 2, execution proceeds to step 210 wherein an energy biasing protocol is implemented as shown in FIG. 4 which applies fuzzy logic Rules 1, 2, and 3 (listed above) to generate a power control signal appropriate for defibrillation.

At step 400 of FIG. 4, a signal identifying a previous biasing value $bias_{defibrillation}$ for defibrillation is retrieved from memory. The value of $bias_{defibrillation}$ is preset to a default value of 90 (indicating that initially 90% of the energy is to be drawn from the SVO cell and 10% from the $CF_x$ cell). At steps 402 and 404, energy source selection is biased toward the SVO cell using fuzzy logic adjustment techniques employing predetermined adjustment factors if the remaining capacity of the $CF_x$ cell is significantly less than that of the SVO cell. To this end, the numeric value of $bias_{defibrillation}$ is adjusted toward 100.

At steps 406 and 408, energy is biased toward the SVO cell based upon the number of years since implant. At steps 410 and 412, energy is biased toward the $CF_x$ cell based upon the number of defibrillation shocks delivered. Steps 406–412 of FIG. 4 are the same as steps 310–316 of FIG. 3 and therefore will not be re-described. However, different adjustment factors may be employed.

At step 414, the value of $bias_{control}$ is set equal to that of $bias_{defibrillation}$ and the value of $bias_{defibrillation}$ is stored. Execution then proceeds to 206 of FIG. 2 wherein $bias_{control}$ is output by the fuzzy logic control unit to the energy source biasing unit for controlling the relative amounts of energy to be drawn from the $CF_x$ and SVO cells for defibrillation. Thus if, after the various adjustments of FIG. 4 have been performed, $bias_{control}$ is ultimately set to a value of 95, then 95% of the energy for the defibrillation is drawn from the SVO cell and 5% is drawn from the $CF_x$ cell.

Figure 5:
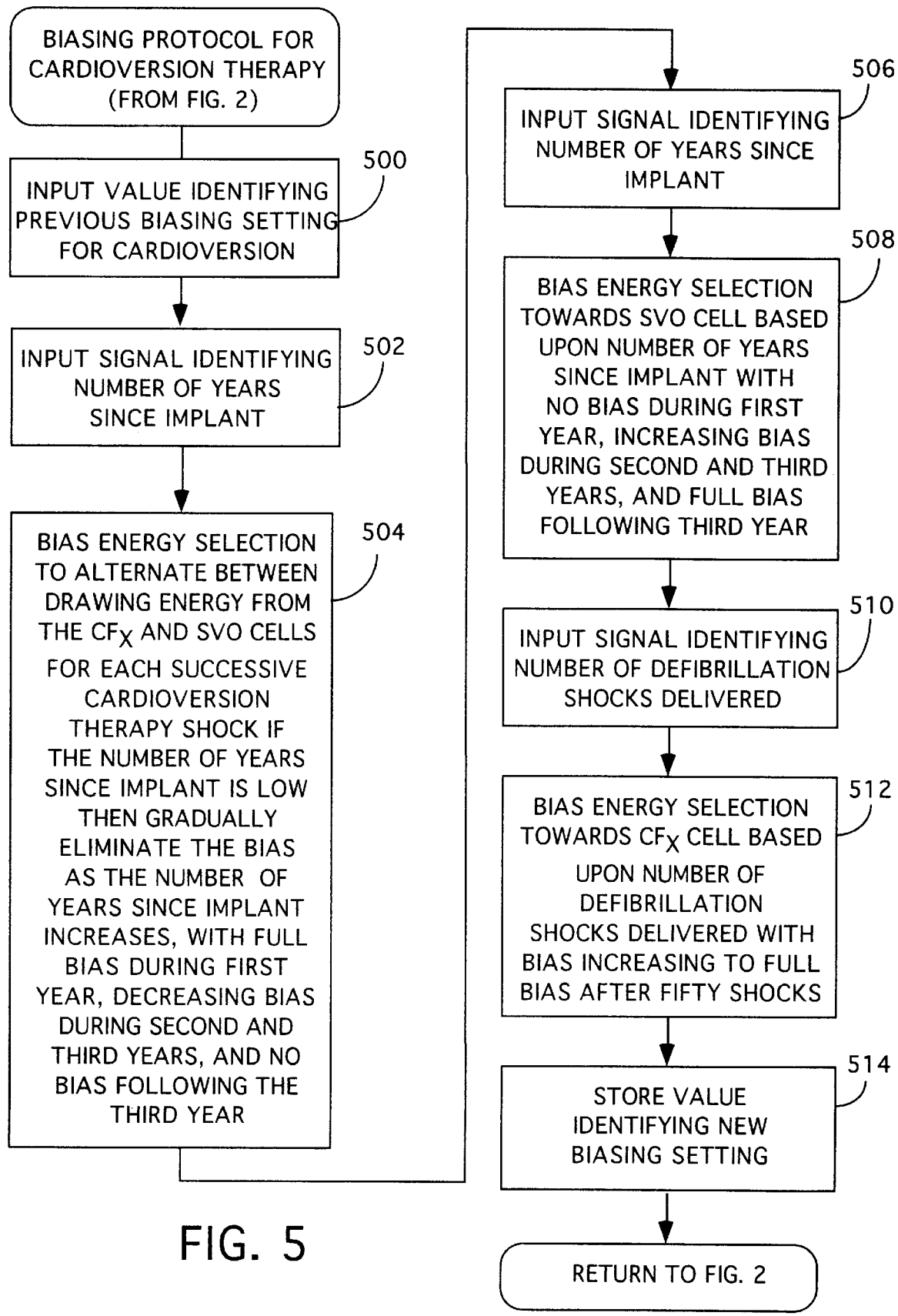
FIG. 5 is a flow chart illustrating particular steps performed for selecting and controlling the relative amounts of energy to be drawn from the pair of power cells for powering cardioversion functions.

If cardioversion is selected then, from step 212 of FIG. 2, execution proceeds to step 214 wherein an energy biasing protocol is implemented as shown in FIG. 5 which applies fuzzy logic Rules 2, 3 and 4 (listed above) to generate a power control signal appropriate for cardioversion.

At step 500 of FIG. 5, a signal identifying a previous biasing value $bias_{cardioversion}$ for cardioversion is retrieved from a memory. The value of $bias_{cardioversion}$ is preset to a default value of 0. At steps 502 and 504, energy source selection is biased to alternate between the SVO cell and the $CF_x$ cell using fuzzy logic adjustment techniques based upon the amount of time since implant of the ICD with the bias toward alternation decreasing during the second and third years and being substantially or completely eliminated after the third year. To this end, the value of $bias_{cardioversion}$ is first reset to (100–biascardioversion) then adjusted upwardly if below 50 and adjusted downwardly if above 50. Hence, if $bias_{cardioversion}$ had been previously set to 2, it is first re-set to 98 then adjusted downwardly, perhaps to 95. If $bias_{cardioversion}$ had been previously set to 97, it is first re-set to 3 then adjusted upwardly, perhaps to 8. In this manner, each subsequent cardioversion shock is drawn either primarily from the SVO cell or primarily from the $CF_x$ cell during the first years after implant in an alternating manner. As the number of years since implant increases, the bias toward alternation decreases until, following step 504, $bias_{cardioversion}$ is set to about 50. As with all biasing operations, the biasing of step 504 is preferably performed using fuzzy logic and by applying pre-determined adjustment factors optimized to achieve enhanced longevity.

At steps 506 and 508, energy is biased toward the SVO cell based upon the number of years since implant. At steps 510 and 512, energy is biased toward the $CF_x$ cell based upon the number of defibrillation shocks delivered. Steps 506–512 of FIG. 5 are the same as steps 310–136 of FIG. 3 and therefore will not be re-described. However, different adjustment factors may be employed.

At step 514, the value of $bias_{control}$ is set equal to that of $bias_{cardioversion}$ and the value of $bias_{cardioversion}$ is stored. Execution then proceeds to 206 of FIG. 2 wherein $bias_{control}$ is output by the fuzzy logic control unit to the energy source biasing unit for controlling the relative amounts of energy to be drawn from the $CF_x$ and SVO cells for cardioversion.

Figure 6:
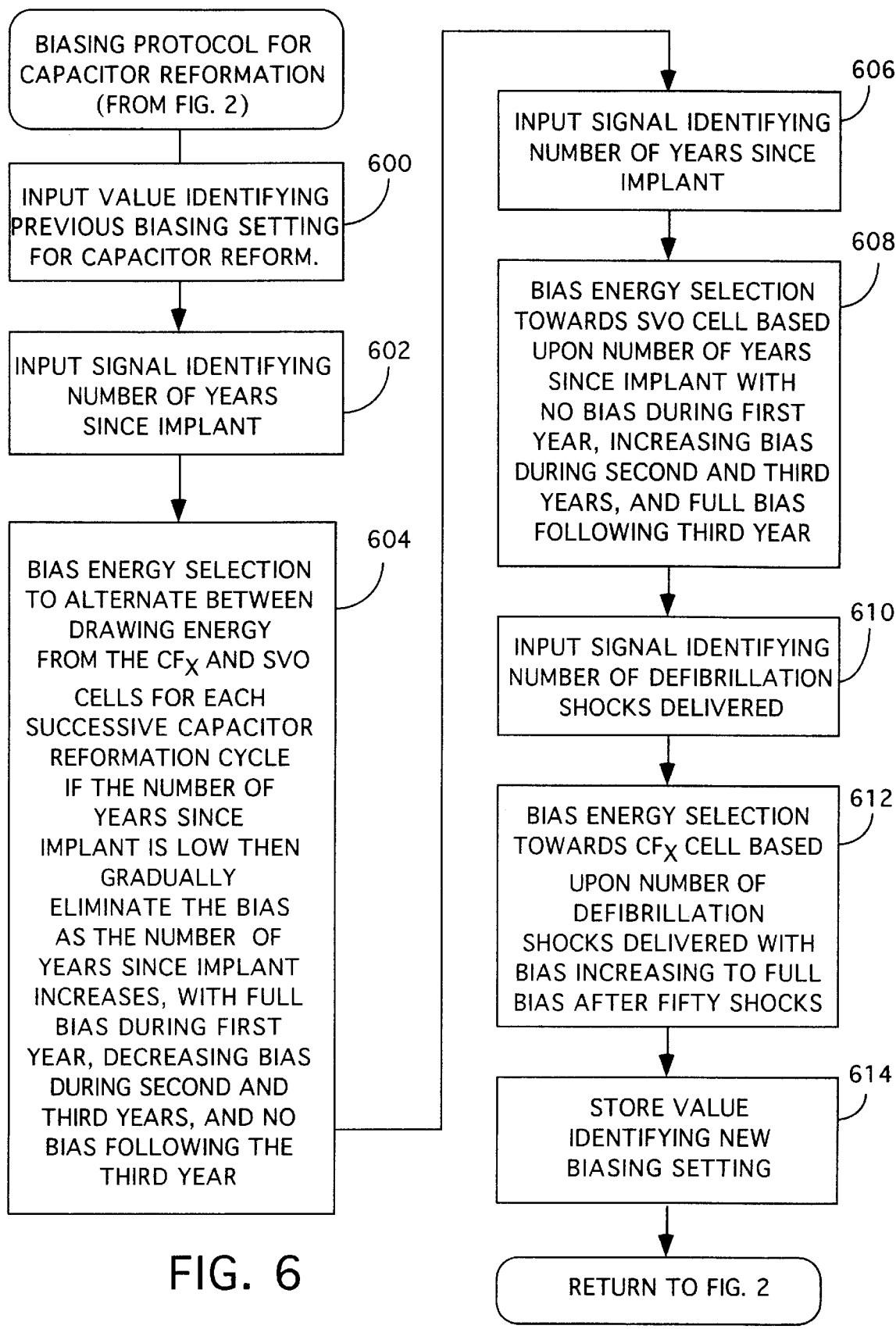
FIG. 6 is a flow chart illustrating particular steps performed for selecting and controlling the relative amounts of energy to be drawn from the pair of power cells for powering capacitor reformation functions.

If capacitor reformation is selected then, from step 216 of FIG. 2, execution proceeds to step 218 wherein an energy biasing protocol is implemented as shown in FIG. 6 which applies fuzzy logic Rules 2, 3 and 4 (listed above) to generate a power control signal appropriate for capacitor reformation.

Figure 7:
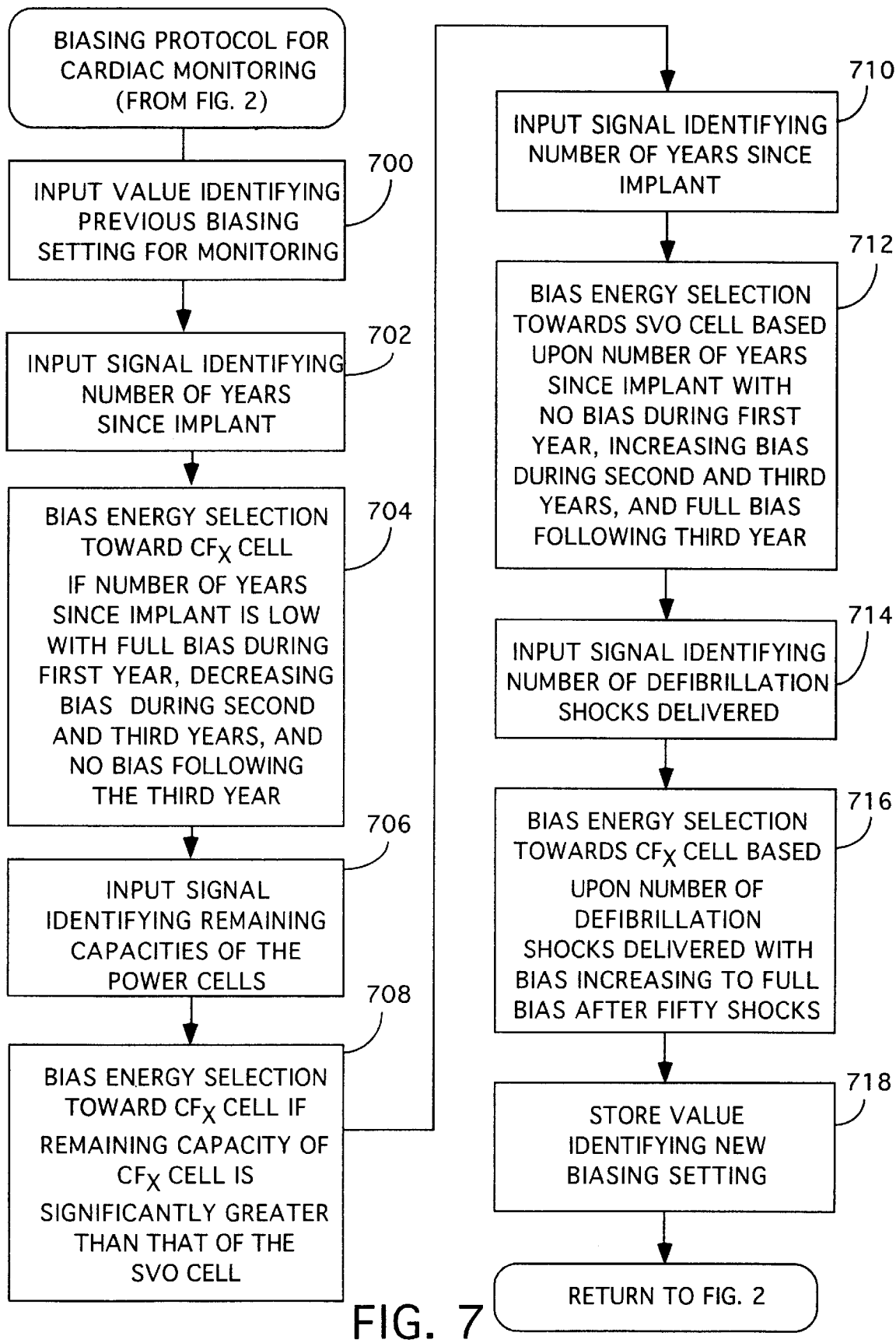
FIG. 7 is a flow chart illustrating particular steps performed for selecting and controlling the relative amounts of energy to be drawn from the pair of power cells for powering cardiac monitoring functions.

Steps 600–612 of FIG. 6 are substantially the same as steps 500–512 of FIG. 7 and will not be re-described. It is worth noting, however, that different adjustment factors may be employed to perform the various biasing operations of FIG. 6 than are employed in connection with FIG. 5.

If cardiac monitoring is selected then, from step 220 of FIG. 2, execution proceeds to step 222 wherein an energy biasing protocol is implemented as shown in FIG. 7 which applies fuzzy logic Rules 2, 3, and 5 (listed above) to generate a power control signal appropriate for monitoring.

At step 700 of FIG. 7, a signal identifying a previous biasing value $bias_{monitoring}$ for monitoring is retrieved from a memory. The value of $bias_{monitoring}$ is preset to a default value of 0 (indicating that initially 100% of the energy is to be drawn from the $CF_x$ cell and 0% from the SVO cell). At steps 702 and 704, energy source selection is biased toward the $CF_x$ cell using fuzzy logic adjustment techniques if the number of years since implant is low. At steps 708 and 710, energy source selection is biased toward the $CF_x$ cell if the remaining capacity of the $CF_x$ cell is significantly greater than that of the SVO cell. At steps 710 and 712, energy is biased toward the SVO cell based upon the number of years since implant. Hence, steps 710 and 712 operate to partially or completely reverse the operation of steps 702 and 704. However, different adjustment factors may be employed such that the reverse bias of steps 710 and 712 is either more than or less than the previous bias of steps 702 and 704. At steps 714 and 716, energy is biased toward the $CF_x$ cell based upon the number of defibrillation shocks delivered. Steps 710–716 of FIG. 7 are the same as steps 310–316 of FIG. 3 but different adjustment factors may be employed.

At step 718, the value of $bias_{control}$ is set equal to that of $bias_{monitoring}$ and the value of $bias_{monitoring}$ is stored. Execution then proceeds to 206 of FIG. 2 wherein $bias_{control}$ is applied to the energy source biasing unit for controlling the relative amount of energy to be drawn from the two power cells for monitoring.

Thus FIGS. 2–7 illustrate the iterative adjustment of power control signals for use in controlling the relative amounts of energy to be drawn from the $CF_x$ and SVO power cells of FIG. 1. As noted, in the exemplary embodiments, iterative adjustment is performed using a fuzzy logic controller configured to process the fuzzy logic rules (listed above). The fuzzy logic controller employs pre-determined adjustment factors set to values intended to optimize overall ICD longevity. The adjustment factors are pre-set either in accordance with theoretically optimal values or in accordance with empirically determined values. In other embodiments, other techniques may be employed for optimizing energy draw in accordance with the general energy allocation principles set forth in the fuzzy logic Rules (listed above) or in accordance with other similar sets of Rules or perhaps in accordance with other completely different energy management protocols that are consistent with the general principles of the invention.

Figure 8:
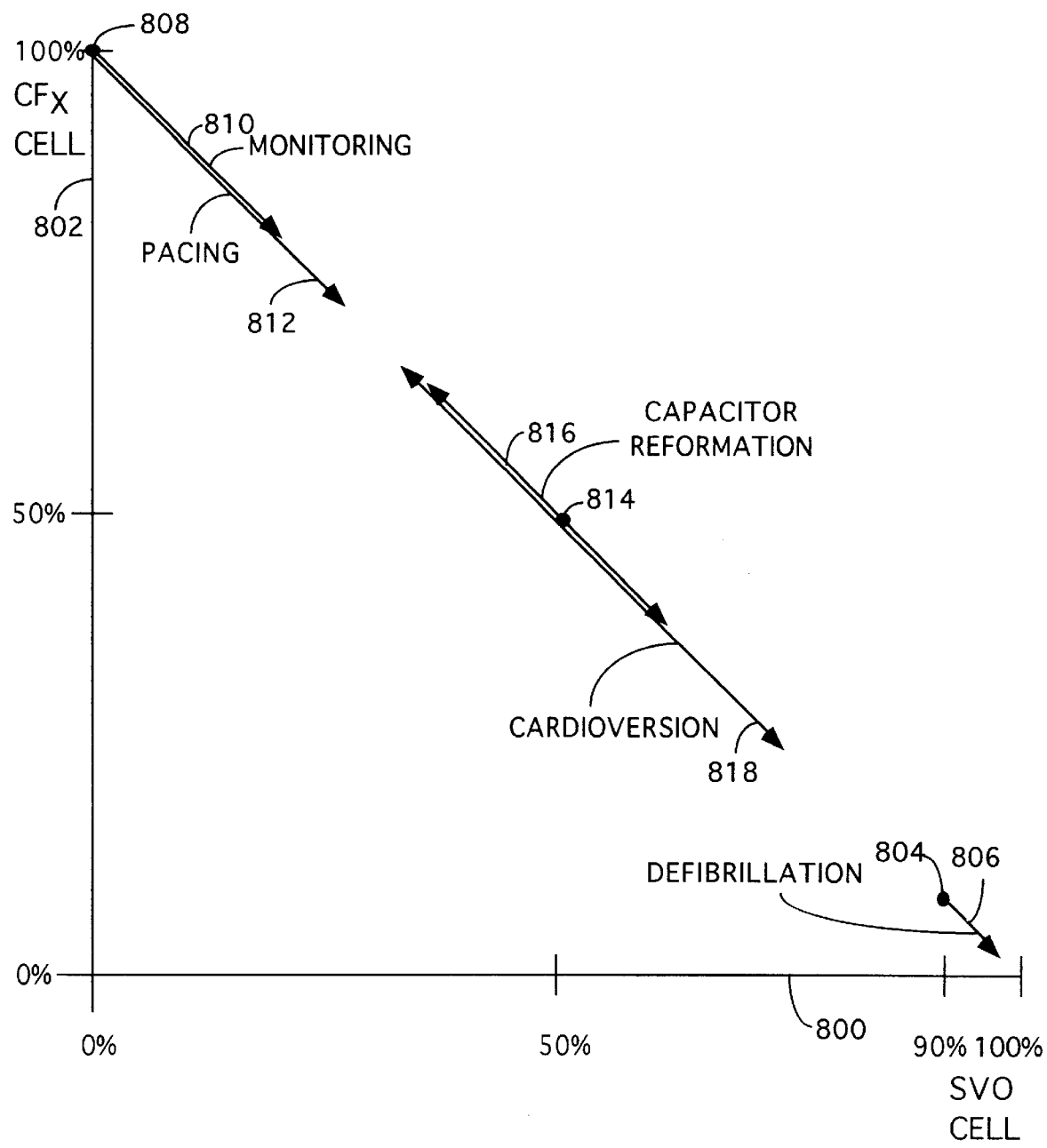
FIG. 8 is a graph illustrating the manner by which relative amounts of energy drawn from the power cells vary with time for various functions when implementing the power control method of FIGS. 2–7.

FIG. 8 graphically illustrates the manner in which the allocation of energy from the $CF_x$ and SVO cells of FIG. 1 typically changes with time as a result of the previously described iterative adjustments. Within FIG. 8, x-axis 800 represents the percentage of energy to be drawn from the SVO cell and y-axis 802 represents the percentage of energy to be drawn from the $CF_x$ cell. For defibrillation, initially energy is drawn at a 90% SVO/10% $CF_x$ ratio as indicated by dot 804. As the number of years since implant increases, a greater percentage of energy is typically drawn from the SVO cell as indicated by line 806. For monitoring, initially energy is drawn at a 0% SVO/100% $CF_x$ ratio as indicated by dot 808. As the number of years since implant increases, a greater percentage of energy is typically drawn from the SVO cell as indicated by line 810. Likewise for pacing, initially energy is drawn at a 0% SVO/100% $CF_x$ ratio as indicated by dot 808. As the number of years since implant increases, a greater percentage of energy is typically drawn from the SVO cell as indicated by line 812. For clarity, line 812 is shown offset slightly from line 810 but both actually lie along the same diagonal. For capacitor reformation, initially energy is drawn alternatingly from either the SVO cell or the $CF_x$ cell resulting in an initial energy allocation of 50% SVO/50% $CF_x$ as indicated by dot 814. As the number of years since implant increases, either a greater percentage of energy is drawn from the SVO cell or a greater percentage is drawn from the $CF_x$ cell as indicated by bi-directional line 816. Likewise for cardioversion, initially energy is drawn alternatingly from either the SVO cell or the $CF_x$ cell as indicated by dot 814. As the number of years since implant increases, either a greater percentage of energy is drawn from the SVO cell or a greater percentage is drawn from the $CF_x$ cell as indicated by bi-directional line 818. For clarity, line 818 is shown as being offset slightly from line 814.

Thus FIG. 8 illustrates the general trend in energy source allocation with time as a result of the adjustments described above in connection with FIGS. 2–7. Depending upon actual changes in the operational parameters of the ICD, any of the general trends shown in FIG. 8 may actually reverse at times. For example, for pacing or monitoring, if the SVO cell begins to be depleted perhaps as a result of frequent defibrillation shocks, the trend toward using greater percentages of energy from the SVO cell for pacing or monitoring will likely begin to reverse. Also, the starting allocations illustrated in FIG. 8 by dots are merely illustrative of typical starting allocations. Again, depending upon the actual conditions, the initial source allocation for any of the functions (other than monitoring) may differ. For example, if the first defibrillation shock is not administered until a significant amount of energy has been depleted from the $CF_x$ cell, then the first defibrillation shock will likely be drawn not a 90% SVO/10% $CF_x$ ratio but at a higher ratio.

Figure 9:
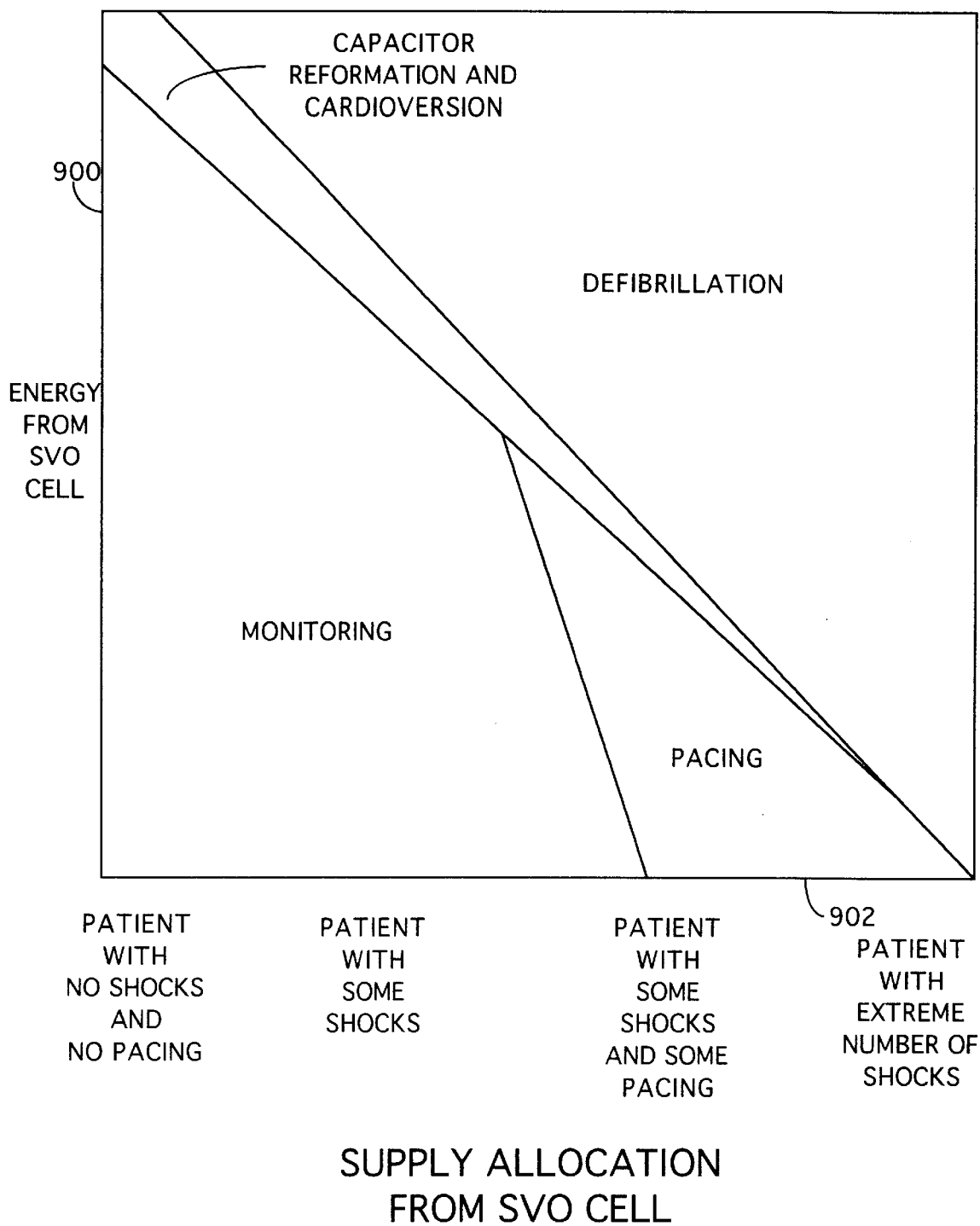
FIG. 9 is a graph illustrating the relative amounts of energy drawn from the $CF_x$ cell for various types of patients when implementing the power control method of FIGS. 2–7.
Figure 10:
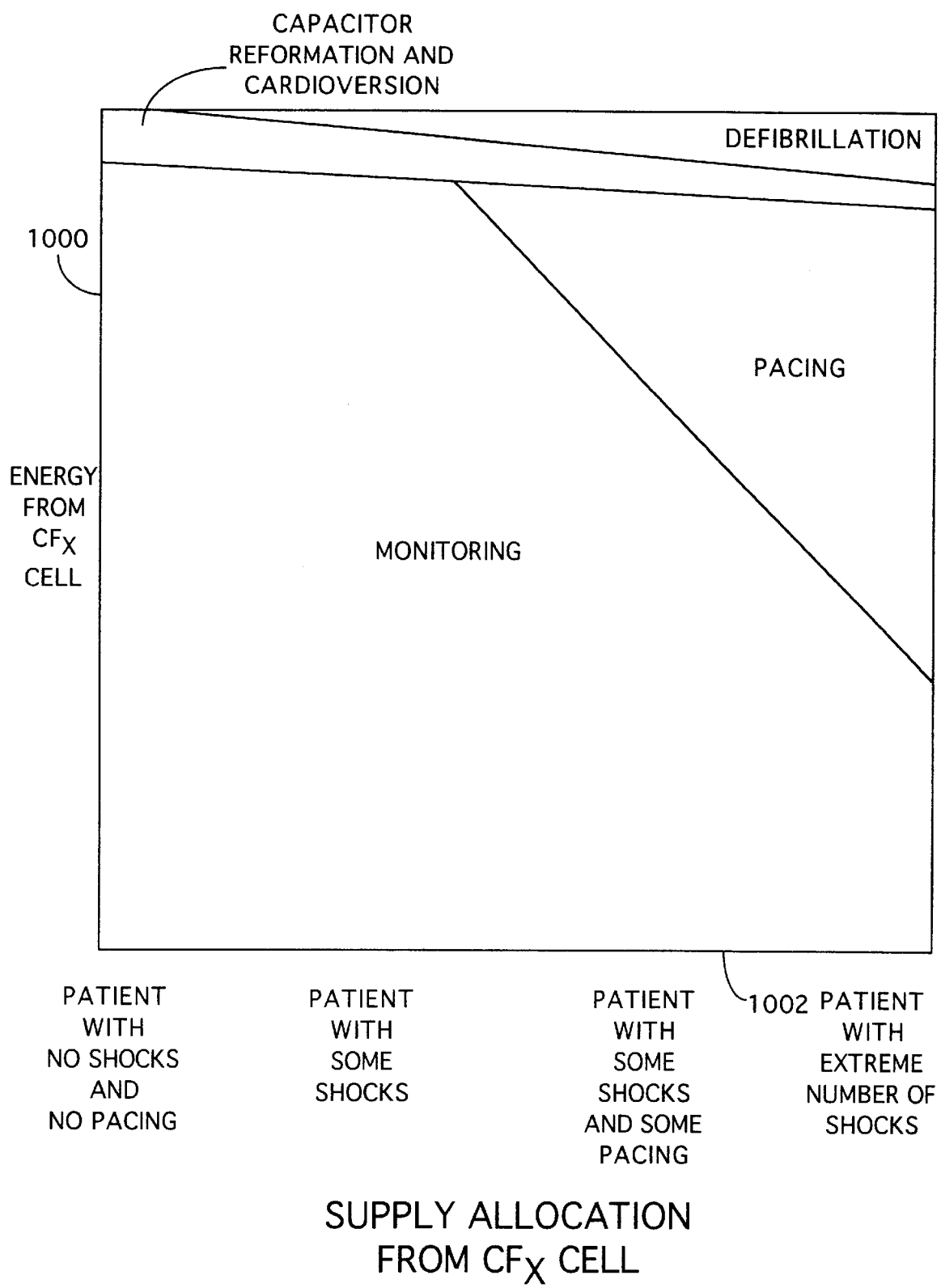
FIG. 10 is a graph illustrating the relative amounts of energy drawn from the SVO cell for various types of patients when implementing the power control method of FIGS. 2–7.

FIGS. 9 and 10 graphically illustrate how energy from the SVO and $CF_x$ cells is typically apportioned to powering different functions for a range or spectrum of different patients.

More specifically, FIG. 9 illustrates energy supply allocation from the SVO cell along a y-axis 900 for a spectrum of patients shown along an x-axis 902 beginning with 1) patients receiving no defibrillation shocks and no pacing; 2) patients receiving some defibrillation shocks; 3) patients receiving some defibrillation shocks and some pacing and finally 4) patients receiving an extreme number of defibrillation shocks. As can be seen, for patients receiving no shocks and no pacing, almost all of the energy from the SVO cell is used for monitoring with only a small amount used for either cardioversion or capacitor reformation. For patients receiving some defibrillation shocks, a portion of the energy from the SVO cell is used for defibrillation, with correspondingly smaller portions for monitoring, cardioversion and capacitor reformation. In this regard, less energy is required for capacitor reformation because the generation of occasional defibrillation shocks begins to obviate the need for reformation cycles. For patients receiving some shocks and some pacing, no energy from the SVO is used for monitoring. Rather, some portion of the energy is drawn for pacing and a still greater portion of energy is drawn for defibrillation. For such patients, all energy for monitoring is typically drawn from the $CF_x$ cell (as will be shown in FIG. 10.) Finally for patients requiring an extreme number of defibrillation shocks, all energy from the SVO cell is allocated to defibrillation. No energy is necessary for capacitor reformation and no energy is available for any other function.

FIG. 10 illustrates energy supply allocation from the $CF_x$ cell along a y-axis 1000 for the same spectrum of patients shown along an x-axis 1002 as shown in FIG. 9. For patients receiving no shocks and no pacing, almost all of the energy from the $CF_x$ cell is used for monitoring with only a small amount for either cardioversion or capacitor reformation. For patients receiving some defibrillation shocks, a portion of the energy from the $CF_x$ cell is used for defibrillation, with correspondingly smaller portions for monitoring, cardioversion and capacitor reformation. For patients receiving some shocks and some pacing, energy from the $CF_x$ cell is primarily used for monitoring and pacing with still smaller amounts for other functions. Finally for patients requiring an extreme number of defibrillation shocks, substantially equal amounts of energy from the $CF_x$ cell are drawn for pacing and monitoring. Very little energy is necessary for capacitor reformation and, since almost all energy from the SVO cell is used for defibrillation, relatively little of the energy available from the $CF_x$ cell is employed for defibrillation.

Thus FIGS. 9 and 10 illustrate the manner by which energy from the two power cells are allocated for a typical range of patients. FIGS. 9 and 10 assume that both power cells have a fair amount of energy. As energy becomes depleted from the cells or as other operational parameters change, the relative amounts of energy allocated to different functions typically varies in accordance with the biasing adjustments described above in connection with FIGS. 2–8.

Figure 11:
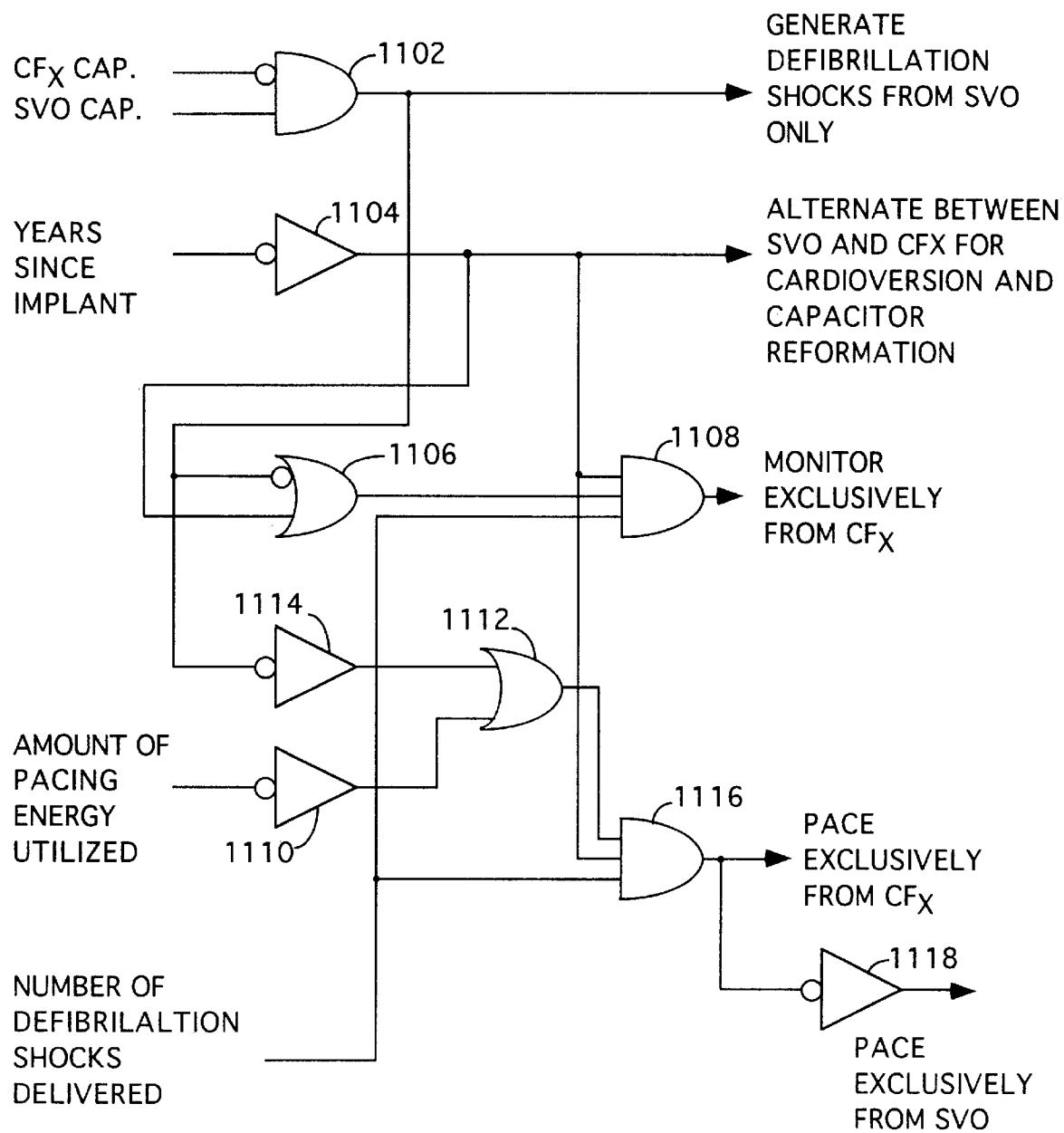
FIG. 11 is a diagram illustrating exemplary logic components appropriate for use within the power control system of FIG. 1 for generating control signals to control the relative amounts of energy drawn from the pair of power cells for various functions.

FIG. 11 illustrates one possible implementation for the logic portion of fuzzy logic controller 34 of FIG. 1 with respect to a set of logical operators. Depending upon the implementation, the logical operators may be simple Boolean logic operators outputting discrete yes/no logic values or may be fuzzy logic operators outputting a range of output values representative of the relative ratio of yes/no. In the following description, it will be assumed that the logic operators are fuzzy logic operators.

The logic of FIG. 11 implements a set of fuzzy logic rules similar to those set forth above as Rules 1–6 but with two exceptions. Whereas Rule 2 (listed above) operates to bias energy draw from the SVO cell based on the number of years since implant for all functions, in the logic of FIG. 11, the number of years since implant is not employed in connection with biasing energy draw for defibrillation. Also, whereas Rule 3 (listed above) operates to bias energy draw toward the $CF_x$ cell based upon the number of shocks delivered for all functions, in the logic of FIG. 11, the number of shocks is not employed in connection with biasing energy for defibrillation, cardioversion or capacitor reformation. Rather, the number of shocks delivered is employed only in connection with biasing energy for pacing and monitoring.

Briefly, AND gate 1102 generates a biasing signal for use increasing the extent to which energy for defibrillation is drawn from the SVO cell in accordance with Rule 1. Inverter 1104 generates a biasing signal for use in decreasing the extent to which energy for cardioversion and defibrillation are alternately drawn from the SVO and $CF_x$ cells in accordance with Rule 4. Outputs of AND gate 1102 and inverter 1104 are combined via OR gate 1106 to yield a biasing signal for use in furtherance of Rule 5. The outputs of OR gate 1106 and inverter 1104 and a signal representative of the number of defibrillation shocks delivered are combined by a three-input AND gate 1108 to yield a signal for biasing the extent to which monitoring energy is drawn from the $CF_x$ cell in accordance with Rule 3 (modified as described). A signal representative of the amount of pacing energy utilized is inverted by inverter 1110 and applied to an OR gate 1112 which also receives the output of inverter 1104 as re-inverted by inverter 1114. OR gate 1112 thereby outputs a signal for use in biasing energy for pacing in furtherance of Rule 6. The output of OR gate 1112, inverter 1104 and the signal representative of the number of defibrillation shocks delivered are all applied to a three-input AND gate 1116 which outputs a signal for biasing the extent to which energy for pacing is drawn exclusively from the $CF_x$ cell in accordance with Rules 2 and 3 (modified as described). Finally, this latter biasing signal is inverted by an inverter 1118 to output a signal for biasing the extent to which energy for pacing is drawn exclusively from the SVO cell, also in accordance with Rule 2 and 3 (modified as described).

Thus FIG. 11 illustrates one possible set of logic gates for use in implementing a set of energy biasing rules. Other configurations are within the scope of the invention. The logic gates may be implemented as hard-wired circuitry or may be emulated by software or by any other appropriate technology for performing logic operations. Hard-wired logic circuitry is preferred to insure that the biasing operations are performed quickly. This is particularly true given that the biasing operations may need to be frequently and repeatedly performed to achieve appropriate iterative adjustments to energy allocation.

Referring again to FIGS. 2–7, depending upon the implementation, the appropriate iterative adjustment may be performed each and every time energy is required for a particular function or may be performed less frequently. Iterative adjustment each time energy is required for a particular functions is desirable for defibrillation, cardioversion and capacitor reformation wherein relatively long periods of time may occur between consecutive iterations during which relatively significant changes in the pertinent operational parameters may occur thereby resulting in meaningful adjustments to the relative amounts of energy to be drawn. However, for pacing and monitoring wherein energy must be drawn frequently if not nearly continuously, it may be preferable to execute the appropriate bias adjustment steps only occasionally. In other words, it may not be necessary or even desirable to repeat all of the bias adjustment steps of FIG. 3 each time a new pacing pulse is required. Rather, it is often appropriate to merely re-use a previously calculated value for $bias_{pacing}$ and to perform the steps needed to readjust $bias_{pacing}$ only once every N pacing pulses, such as every 1000 pulses, or perhaps only once per day, week or month. Likewise, for monitoring, which is continuously performed unless some other function is required, it may be appropriate to perform the steps of FIG. 7 to re-adjust the energy bias for monitoring ($bias_{monitoring}$) only every few weeks or months.

Hence, FIGS. 2–7 operate to generate an energy bias control signal for applying to energy source biasing unit 36 of FIG. 1 wherein the control signal specifies the relative amounts of energy to be drawn from the $CF_x$ and SVO power cells. Depending upon the implementation of the energy source biasing unit, the control signal may further specify the total amount of energy to be supplied for the selected function and also the functional unit to which the energy is to be directed.

In the present exemplary embodiment, the energy source biasing unit includes two separate power control switches (not shown) connected respectively to the $CF_x$ and SVO cells which, when closed, operate to draw energy from the respective power cell. The energy source biasing unit also includes a set of switches (also not shown) for routing the energy drawn from the power cells to the selected functional unit. The power control signal that is output from fuzzy logic controller 34 (FIG. 1) is based upon $bias_{control}$ (FIG. 2) but includes a separate power control signal for the $CF_x$ cell, a separate power control signal for the SVO cell, and a separate signal specifying the functional unit to receive the energy. The two separate power control signals are applied to the two separate power control switches for differing periods of time depending upon the value of $bias_{control}$, the total amount of energy to be drawn and the relative impedances of the two power cells. More specifically, the total amount of time each power control signal is applied to its respective power control switch is set in accordance with the total amount of energy to be drawn from that respective power cell. The difference, if any, between the length of time the two signals are applied to the two power control switches is set in accordance with $bias_{control}$ and in accordance with the relative impedances of the two cells.

For example, as far as relative energy source allocation is concerned, if $bias_{control}$ is 50 (indicating that equal amounts of energy are to be drawn) and the ratio of impedance between the SVO and $CF_x$ cells is 1:1, then the individual control signals are applied for equal amounts of time to the two power control switches to draw equal amounts of energy from the two cells. If $bia_{control}$ is 50 and the ratio of impedances between the SVO and $CF_x$ cells is 9:1, then the individual control signals are applied for time periods at a ratio of 9:1 to draw equal amounts of energy from the two cells. If $bias_{control}$ is 25 (indicating that 75% of the energy is to be drawn from the SVO cell and 25% of the energy is to be drawn from the $CF_x$ cell) and the ratio of impedance between the SVO and $CF_x$ cells is 1:1, then the individual control signals are applied for time periods at a ratio of 1:4 to draw energy at a ratio to 1:4.

As far as the total amount of energy to be drawn is concerned, if a defibrillation pulse requires twenty joules of energy and a cardioversion pulse requires two joules, all other factors being equal, the power control signals will be applied to the power control switches for, for example, twenty seconds for defibrillation and two seconds for cardioversion.

As can be appreciated, a wide range of other techniques may be employed for generating control signals for specifying both the relative and the actual amounts of energy to be drawn from the two power cells.

What has been described is a technique for selecting the relative amount of energy to be drawn from a pair of power cells within an ICD for powering various different functions. Principles of the invention may be applied in other applications as well. For example, principles of the invention may be applicable to other implantable devices or to devices having more than two different energy sources. Hence, the embodiments described herein should be regarded as being merely illustrative of the invention and should not be construed as limiting the scope of the invention.

What is claimed is:

1. In an implantable medical device having two or more different energy sources for powering two or more different device functions, a power control system comprising:

means for receiving signals representative of an operational status of the implantable medical device;

means for biasing relative amounts of energy drawn from the two or more different energy sources; and means for controlling the means for biasing to gradually vary the relative amounts of energy drawn from the two or more different energy sources based upon the signals representative of the operational status of the implantable medical device.

2. The power control system of claim 1:

wherein the two or more device functions include at least two functions selected from a group including cardioversion therapy, cardiac defibrillation, capacitor reformation, cardiac pacing and cardiac monitoring; and wherein the two or more energy sources include a first power cell optimized for providing continuous low-power and a second power cell optimized for providing infrequent bursts of high power.

3. The power control system of claim 2, wherein the first power cell is a carbon monofluoride cell and the second power cell is a silver vanadium oxide cell.

4. The power control system of claim 2, wherein the means for controlling applies fuzzy logic to the signals representative of the operational status of the implantable medical device to control the means for biasing to gradually adjust the relative amounts of energy drawn from the first and second power cells.

5. The power control system of claim 2, wherein the means for controlling applies the following fuzzy logic rules:

a) defibrillation shocks are simultaneously drawn from the first and second power cells unless the remaining capacity of the first power cell is much less than that of the second power cell;

b) a greater amount of energy is drawn from the second power cell than from the first power cell if the amount of time since implant is high;

c) a greater amount of energy is drawn from the first power cell than from the second power cell if the number of defibrillation shocks is high;

d) energy is alternatingly drawn from the first and second cells for capacitor reformation and for cardioversion therapy during the first few years since implant;

e) monitoring energy is drawn from the first cell during the first few years after implantation or when the remaining capacity of the first cell is significantly greater than that of the second cell; and f) pacing energy is drawn from the first cell when relatively little pacing energy has been used or if the remaining capacity of the first cell is significantly greater than that of the second cell.

6. The power control system of claim 2, wherein the means for receiving signals representative of an operational status of the implantable medical device includes:

means for receiving input function signals identifying one or more selected device functions to be performed by the implantable medical device; and means for receiving input status signals from a group including signals representative of remaining capacities of the first and second power cells, an amount of time since implant of the implantable device, a number of defibrillation shocks delivered, and an amount of pacing energy previously utilized.

7. The power control system of claim 6:

wherein the selected device function is defibrillation and the input status signals identify remaining capacities of the first and second power cells; and wherein the means for controlling operates to control the means for biasing to simultaneously draw energy from both the first and second cells in a predetermined ratio unless the capacity of the first cell is significantly less than that of the second cell wherein the means for biasing is then controlled to draw energy only from the second cell.

8. The power control system of claim 6:

wherein the selected device function is any of the functions and the input status signals identify the amount of time since implant; and wherein the means for controlling operates to control the means for biasing to bias energy source selection toward the second cell based upon the amount of time from implantation.

9. The power control system of claim 6:

wherein the selected device function is any of the functions and wherein the input status signals identify the number of defibrillation shocks delivered; and wherein the means for controlling operates to control the means for biasing to bias energy source selection toward the first cell based upon the number of defibrillation shocks delivered.

10. The power control system of claim 6:

wherein the selected device function is capacitor reformation and the input status signals identify the amount of time since implant; and wherein the means for controlling operates to control the means for biasing to initially draw energy alternately between the first and second power cells upon implantation of the device and to subsequently gradually eliminate such bias.

11. The power control system of claim 6:
wherein the selected device function is cardioversion therapy and the input status signals identify the amount of time since implant; and
wherein the means for controlling operates to control the means for biasing to initially bias energy source selection alternately between the first and second power cells and to subsequently eliminate said bias as a function of the amount of time since implant.

12. The power control system of claim 6:
wherein the selected device function is cardiac monitoring and the input status signals identify the amount of time since implant; and
wherein the means for controlling operates to control the means for biasing to initially bias energy source selection toward the first cell and to subsequently eliminate said bias as a function of the amount of time since implant.

13. The power control system of claim 6:
wherein the selected device function is cardiac monitoring and the input status signals identify the remaining capacities of the first and second cells; and
wherein the means for controlling operates to control the means for biasing to bias energy source selection toward the first cell while the capacity of the first cell is significantly greater than that of the second cell.

14. The power control system of claim 6:
wherein the selected device function is cardiac pacing and the input status signals identify the amount of pacing energy utilized; and
wherein the means for controlling operates to control the means for biasing to initially bias energy source selection toward the first cell and to subsequently eliminate said bias as greater amounts of pacing energy have been utilized.

15. The power control system of claim 6:
wherein the selected device function is cardiac pacing and the input status signals identify the remaining capacities of the first and second power cells; and
wherein the means for controlling operates to control the means for biasing to bias energy source selection toward the first cell if the remaining capacity of the first cell is significantly greater than that of the second cell.

16. The power control system of claim 1, wherein the implantable medical device is a cardioverter defibrillator.

17. In an implantable medical device having two or more energy sources for powering two or more device functions, a power control system comprising:
means for receiving signals representative of an operational status of the implantable medical device; and
means for selectively varying the relative amounts of energy drawn from the two or more energy sources for powering the two or more device functions by applying fuzzy logic to the signals representative of an operational status of the implantable medical device.

18. In an implantable medical device having first and second energy sources for powering two or more device functions, a power control system comprising:
means for biasing relative amounts of energy drawn from the first and second energy sources; and
means for controlling the means for biasing to switch from the first energy source to the second energy source for powering a selected one of said functions and then to switch back to the first energy source for further powering of said selected device function.

19. In an implantable medical device having a low-power cell and a high-power cell for powering pacing functions, a power control system comprising:
means for biasing the relative amounts of energy drawn from the low-power and high-power cells; and
means for controlling said means for biasing to initially draw energy from the low-power cell for powering the pacing functions and to subsequently switch from the low-power cell to the high-power cell to further energy the pacing functions as energy in the low-power cell becomes depleted.

20. In an implantable medical device having two or more different energy sources for powering two or more different device functions, a power control method comprising the steps of:
receiving signals representative of an operational status of the implantable medical device;
gradually varying relative amounts of energy drawn from the two or more different energy sources based upon the signals representative of the operational status of the implantable medical device.

21. The power control method of claim 20:
wherein the two or more device functions include at least two functions selected from a group including cardioversion therapy, cardiac defibrillation, capacitor reformation, cardiac pacing and cardiac monitoring; and
wherein the two or more energy sources include a first power cell optimized for providing continuous low-power and a second power cell optimized for providing infrequent bursts of high-power.

22. The power control method of claim 20, wherein the step of gradually varying the relative amounts of energy drawn from the two or more different energy sources is performed by applying fuzzy logic to the signals representative of the operational status of the implantable medical device to generate control signals for biasing the relative amounts of energy drawn from the first and second power cells.

23. The power control method of claim 22, wherein the step of gradually varying the relative amounts of energy drawn from the two or more different energy sources is performed by applying the following fuzzy logic rules
a) defibrillation shocks are simultaneously drawn from the first and second power cells unless the remaining capacity of the first power cell is much less than that of the second power cell;
b) a greater amount of energy is drawn from the second power cell than from the first power cell if the amount of time since implant is high;
c) a greater amount of energy is drawn from the first power cell than from the second power cell if the number of defibrillation shocks is high;
d) energy is alternatingly drawn from the first and second cells for capacitor reformation and for cardioversion therapy during the first few years since implant;
e) monitoring energy is drawn from the first cell during the first few years after implantation or when the remaining capacity of the first cell is significantly greater than that of the second cell;
f) pacing energy is drawn from the first cell when relatively little pacing energy has been used or if the remaining capacity of the first cell is significantly greater than that of the second cell.

24. In an implantable medical device having two or more different energy sources for powering two or more different device functions, a power control system comprising:
- a device status input unit for receiving signals representative of an operational status of the implantable medical device;
- a selected function input unit for receiving signals representative of one or more selected functions to be performed by the implantable medical device;
- an energy source biasing unit for biasing relative amounts of energy drawn from the two or more different energy sources; and
- a fuzzy logic controller unit for controlling the energy source biasing unit to vary the relative amounts of energy drawn from the two or more different energy sources based upon the signals representative of the selected device function and the operational status of the implantable medical device.

* * * * *